United States Patent [19]
Mori et al.

[11] Patent Number: 5,649,907
[45] Date of Patent: Jul. 22, 1997

[54] DEVICE FOR DISSOLVING AND DELIVERING A DRUG IN A TRANSFUSION LIQUID

[75] Inventors: Kenji Mori, 2041-1, Naka, Tamana-shi, Kumamoto-ken; Yoshiaki Akaike, Yamanashi-ken, both of Japan

[73] Assignees: Kenji Mori, Kumamoto-ken; Terumo Kabushiki Kaisha, Tokyo, both of Japan

[21] Appl. No.: 494,488

[22] Filed: Jun. 26, 1995

[30] Foreign Application Priority Data

Jun. 27, 1994 [JP] Japan ................. 6-009346 U

[51] Int. Cl.$^6$ ................................................. A61M 37/00
[52] U.S. Cl. .......................... 604/85; 604/82; 604/262; 604/403; 604/408; 604/414
[58] Field of Search ................. 604/85, 19, 80, 604/82, 83, 86, 87, 88, 89, 257, 262, 403, 408, 410, 411, 414, 415, 416

[56] References Cited

U.S. PATENT DOCUMENTS

| | | |
|---|---|---|
| 4,804,366 | 2/1989 | Zdeb et al. . |
| 4,936,829 | 6/1990 | Zdeb et al. . |
| 5,024,657 | 6/1991 | Needham et al. . |

*Primary Examiner*—Michael Powell Buiz
*Assistant Examiner*—N. Kent Gring
*Attorney, Agent, or Firm*—Frishauf, Holtz, Goodman, Langer & Chick

[57] ABSTRACT

A device for dissolving and delivering a drug in a transfusion liquid includes a transfusion liquid container, a drip chamber, a transfusion tube communicating with the drip chamber, and a cylindrical body having first and second end portions. The cylindrical body is communicable with the container at the first end portion, and with the drip chamber at the second end portion. A first hollow needle communicates with, and projects outwardly from, the cylindrical body. The first needle establishies communication between the container and a drug container containing a drug to be introduced into the transfusion liquid, through the cylindrical body, by piercing into the drug container. A drug container is accommodated in an accommodating member provided on the cylindrical body. A movable valve body is provided inside the cylindrical body at an initial position at which its side portion does not clog the first needle. The valve defines a space through which the transfusion liquid is introduced into the drug container to dissolve the drug when the cylindrical body communicates with the transfusion liquid container and the drug container is accommodated into the accommodating body and pierced by the first hollow needle. A second hollow needle communicates with the drip chamber and can advance into the cylindrical body. The second needle establishes communication between the drip chamber and the container by piercing the valve after the dissolved drug is introduced into the container.

10 Claims, 4 Drawing Sheets

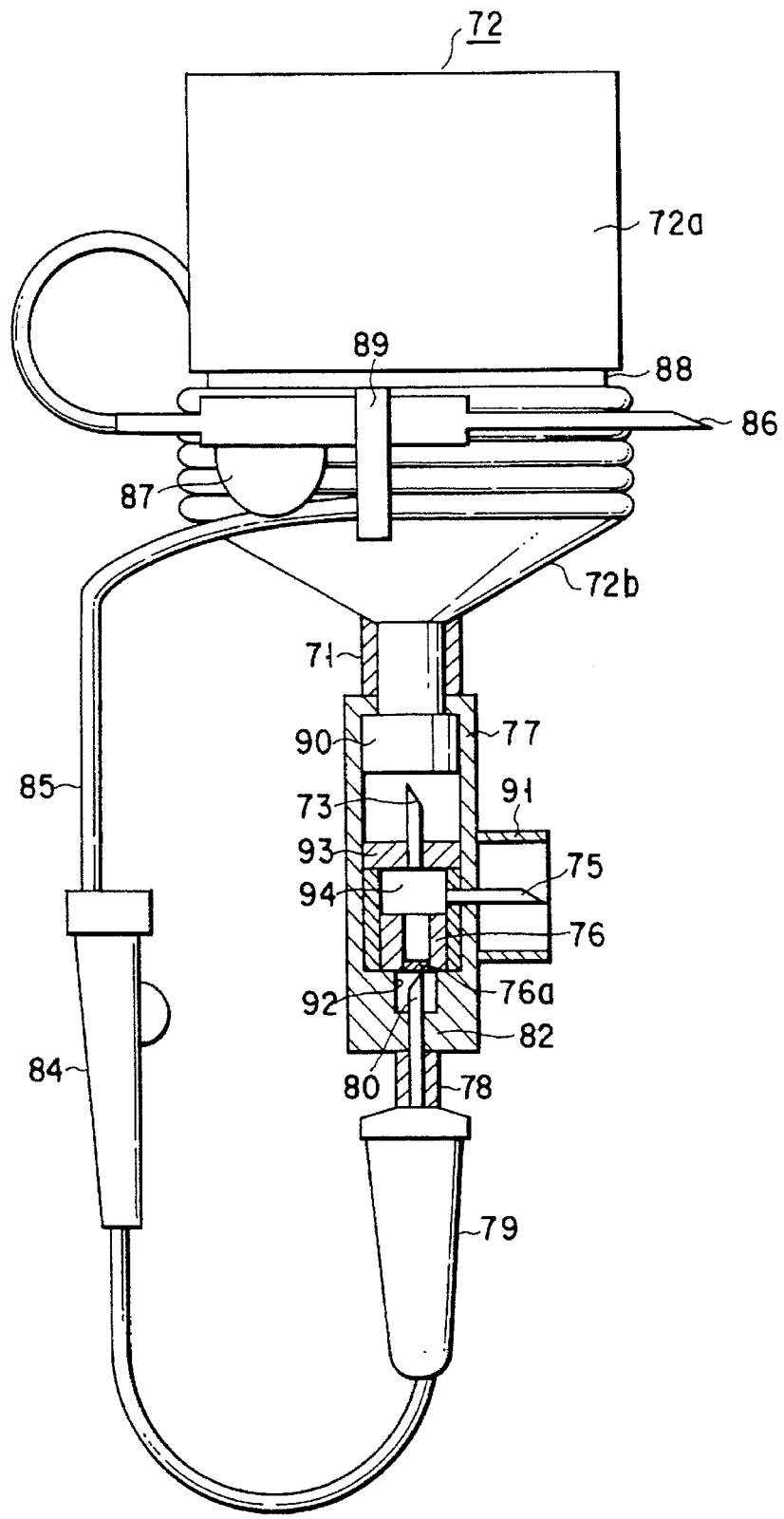
F I G. 3

DEVICE FOR DISSOLVING AND DELIVERING A DRUG IN A TRANSFUSION LIQUID

BACKGROUND OF THE INVENTION

1. Field of the Invention

The present invention relates to a drug delivering device having a mechanism for dissolving a drug in a transfusion liquid which is administered to a subject.

2. Description of the Related Art

Intravenously administered drugs are usually given to a patient or subject after they are dissolved in a transfusion liquid. Generally, many drugs are provided in the form of powder contained in a container such as a vial. To date, very laborious or time-consuming operations have been taken to ultimately introduce powdery drugs into the transfusion liquid. Specifically, a portion of the transfusion liquid is sucked in a syringe, and injected into a vial which contains the powdery drug to partially dissolve the drug in the injected liquid. Such a sucking operation and injecting/dissolving operations are repeated, until all of the powdery drug is introduced into the transfusion liquid. These operations need to be done under sterile conditions, but it is difficult to maintain a sterile state during such complicated operations.

Devices which allow for a simplified dissolving operation of drugs are disclosed in, for example, U.S. Pat. Nos. 4,804,366; 4,936,829; and 5,024,657. However, there still exists a need for a drug delivering device having a mechanism for dissolving a drug in a transfusion liquid under sterile conditions and delivering the drug together with the transfusion to a subject.

SUMMARY OF THE INVENTION

It is therefore an object of the present invention to provide a drug delivery device having a mechanism for easily dissolving a drug in a transfusion liquid, which is administered to a subject in the dissolved state.

According to the present invention, there is provided a device for dissolving and delivering a drug comprising:

a transfusion liquid container containing a transfusion liquid;

a drip chamber;

a tansfusion tube communicating with the drip chamber;

a cylindrical body having first and second end portions, the cylindrical body communicable with the inside of the transfusion liquid container at the first end portion, and with the drip chamber at the second end portion;

a first hollow needle communicating with, and projecting outwardly from, the cylindrical body, the first hollow needle establishing communication between the transfusion liquid container and a drug container containing a drug to be introduced into the transfusion liquid, through the cylindrical body, by piercing into the drug container;

a drug container-accommodating or holding body provided around the first hollow needle and outside the cylindrical body, for accommodating or holding the drug container;

a movable valve body having a side portion liquid tightly slidable on the inner surface of the cylindrical body, and provided inside the cylindrical body at an initial position at which the side portion does not close the first hollow needle, the movable valve body defining a space through which the transfusion liquid is introduced into the drug container to dissolve the drug when the cylindrical body communicates with the transfusion liquid container and the drug container is accommodated into the accommodating body and pierced by the first hollow needle; and a second hollow needle which communicates with the drip chamber and is capable of advancing into the cylindrical body under sterile conditions, the second hollow needle establishing communication between the drip chamber and the transfusion liquid container by piercing the valve body after the dissolved drug is introduced into the transfusion liquid container, and moving the valve body from the initial position to a second position at which the first hollow needle is closed by the side portion of the valve body.

In a first embodiment of the present invention, the movable valve has a plurality of annular ribs on the side surface which slidably contacts the inner surface of the cylindrical body.

In the present invention, the cylindrical body may have a first connecting tube on its upper end portion, and the transfusion liquid container may have a second connecting tube. The first and second connecting tubes may be joined under sterile conditions. In this case, a communicating mechanism may be provided in the second connecting tube, which mechanism establishing communication between the transfusion liquid container and the cylindrical body by cutting off the mechanism. Further, a sterility-maintaining gasket may be provided on the proximal end of the second hollow needle.

According to a second embodiment, the movable valve body may be formed of a hollow cylinder having an upper open end and a closed bottom end which may be pierced by the second hollow needle. In a preferred embodiment, the transfusion liquid container or the cylindrical body has a means for accommodating the tansfusion tube. The accommodating means may comprise a groove.

According to the present invention, there is further provided a device for dissolving and delivering a drug comprising:

a drip chamber;

a tansfusion tube communicating with the drip chamber;

a cylindrical body having first and second end portions, the cylindrical body communicable with the inside of a transfusion liquid container containing a transfusion liquid at the first end portion, and with the drip chamber at the second end portion;

a first hollow needle communicating with, and projecting outwardly from, the cylindrical body, the first hollow needle establishing communication between a drug container containing a drug to be introduced into the transfusion liquid, through the cylindrical body, by piercing into the drug container;

a drug container-accommodating or holding body provided around the first hollow needle and outside the cylindrical body, for accommodating or holding the drug container;

a movable valve body having a side portion liquid tightly slidable on the inner surface of the cylindrical body, and provided inside the cylindrical body at an initial position at which the side portion does not close the first hollow needle, the movable valve body defining a space through which the transfusion liquid is introduced into the drug container to dissolve the drug when the cylindrical body communicates with the transfusion liquid container and the drug container is accommodated into the accommodating body and pierced by the first hollow needle; and a second hollow needle which communicates with the drip chamber and is capable of advancing into the cylindrical body under sterile conditions, the second hollow needle establishing communication between the drip chamber and the transfusion liquid container by piercing the valve body after the dissolved drug is introduced into the transfusion liquid container, and moving the valve body from the initial position to a second position at which the first hollow needle is closed by the side portion of the valve body.

BRIEF DESCRIPTION OF THE DRAWINGS

FIG. 3 schematically shows a drug delivery device according to a third embodiment of the present invention;

DETAILED DESCRIPTION OF THE PREFERRED EMBODIMENTS

The present invention will now be described in detail with reference to the accompanying drawings.

Figure 1:
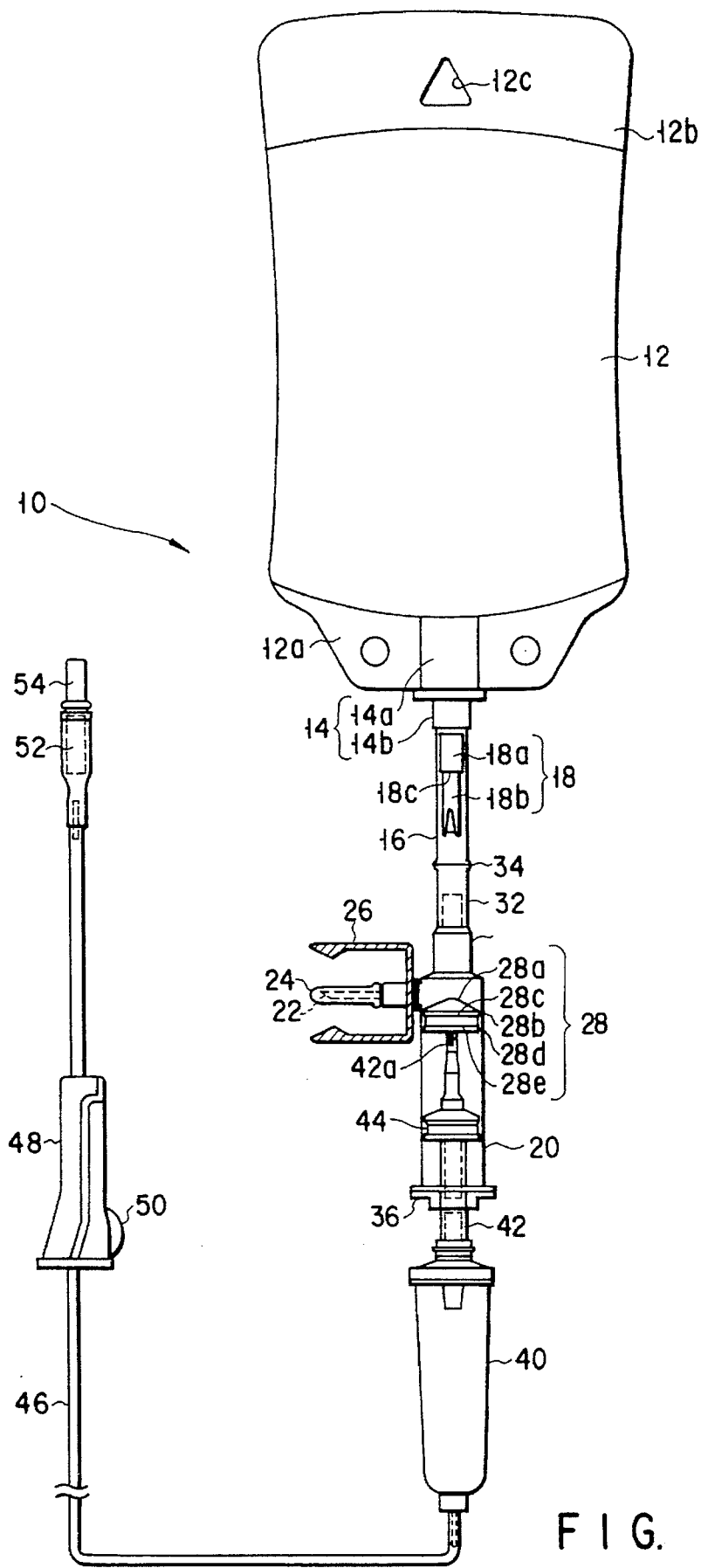
FIG. 1 schematically shows a drug delivery device according to a first embodiment of the present invention.

FIG. 1 show a drug delivery device 10 according to a first embodiment of the present invention.

The device 10 includes a transfusion liquid bag 12 made of a soft plastic material, and containing a transfusion liquid such as a glucose solution or a physiological saline. The bag 12 has a discharge port 14 for the transfusion liquid. The discharge port 14 penetrates a first fused end portion 12a of the bag 12. At a second fused end portion 12b of the bag 12, a through hole 12c is provided which is hooked by a suitable hook member of a suspending tool for the bag 12.

The port 14 has a forward end portion 14b having a smaller diameter than a body portion 14a of the port 14. The smaller diameter portion 14b communicates with a soft tube 16 for sterile connection.

In the tube 16, there is provided a communication member 18 which establishes communication between the tube 16 and the bag 12 via the port 14 at any desired time. The communication member 18 is formed of a relatively hard short tube 18a which is connected with the smaller diameter portion 14b of the port 14, and a solid piece 18b formed integrally with the short tube 18a. The short tube 18a has an outer diameter substantially equal to the inner diameter of the tube 16, but the piece 18b has a flattened shape. At the joined portion of the short tube 18a and the piece 18b, there is formed a thin portion 18c at which the communication member 18 may be cut to separate the piece 18b from the short tube 18a. The short tube 18a is made open to establish communication between the tube 16 and the bag 12 via the port 14 by manually cutting the communication member 18 at the thin portion 18c from outside.

The drug delivery device of the present invention further includes, in addition to the transfusion liquid bag 12, a mechanism which can easily and sterilely dissolving a drug which is usually in a powder form and supplied in a hard container such as a vial. The drug dissolving mechanism has a round hollow cylindrical body 20 generally made of a relatively hard plastic material. On the upper portion of the cylindrical body 20, there is provided a hollow needle 22 which establishes communication between the cylindrical body 20 and the vial containing powdery drug by piercing the rubber stopper of the vial. An elastic cap 24 covers the needle 22.

Around the needle 22, there is provided a cup-shaped accommodating member 26 for accommodating and holding the vial when the rubber stopper of the vial is pierced by the needle 22.

A movable valve body 28 is provided within the cylindrical body 20. The valve body 28 has a side portion which can slidably contact the inner surface of the cylindrical body 20. More specifically, the valve body 28 is constructed by a hollow conical head 28a fitting with the inner surface of the tip end portion of the cylindrical body 20, and a hollow cylindrical trunk 28b formed integrally with the conical head 28a and having an outer diameter smaller than the inner diameter of the cylindrical body 20. Annular ribs 28c and 28d which can slidably contact the inner surface of the cylindrical body 20 are formed on the joining portion of the head 28a and trunk 28b and on the rear end portion of the trunk 28b, respectively. The lower open end of the trunk 28b is closed by a thin film 28e which can be pierced by a needle. The valve body 28 is placed at an initial position at which the side surface of the valve body 28 does not clog the hollow needle 22.

A cap 36 is provided on the lower open end of the cylindrical body 20. On the upper end of the cylindrical body 20, a hard short tube 30 communicating with the cylindrical body 20. Further, a connecting tube 32 is provided fitting over the short tube 30, sterilely joined to the connecting tube 16 at a portion 34. Meanwhile, the transfusion liquid within the bag 12 is usual subjected to the autoclave sterilization, while the transfusion set including cylindrical body 20, a drip chamber hereinafter described and the like is subject to a sterilization by gamma-rays or ethylene oxide gas. If the transfusion liquid bag 12 is coupled to the transfusion set, the desired sterilization can not be conducted. Therefore, the connecting tubes 16 and 32 are joined sterilely by the use of a sterile joining device commercially available from TERUMO CORPORATION of Japan under the tradename of CAPDEAL TSCD.

The drug delivery device of the invention further comprises a drip chamber 40. The drip chamber 40 has a tube 42 made of a hard plastic material and communicating with the inside of the chamber 40. The tube 42 penetrates the cap 36 and is extended into the cylindrical body 20. The tube 42 can move forwardly and backwardly within the cylindrical body 20 by manipulation of the drip chamber 40. More specifically, the tube can be moved by forcing it into or from the cylindrical body 20 with the use of one hand while the drip chamber 40 is held by another hand. The tip end portion of the tube 42 forms a hollow needle 42a which ultimately establishes communication between the drip chamber 40 and the bag 12 by piercing the valve body 28. Further, within the cylindrical body 20, a sterility-maintaining gasket 44 is provided, with the tube 42 penetrating therethrough. The gasket 44 prevents bacteria from invading into the cylindrical body 20.

At the rear end of the drip chamber 40, a usual transfusion tube 46 is provided, and a clamp 48 is provided which regulates the flow rate of the transfusion liquid by a roller 50. At the tip end portion of the tube 46, there is provided luar connector 52, on which a cap 54 with a filter is attached.

To dissolve the powdery drug in the vial in the transfusion liquid in the bag 12, the vial is accommodated in the accommodating member 26, and the rubber stopper of the vial is pierced by the hollow needle 22. Then, the communication mechanism 18 is cut off at the thin portion 18c with fingers to open the short tube 18b. Next, the pressure is exerted on the bag 12, for example, by collapsing the bag 12 with a hand, to send a transfusion liquid in the bag 12 to the vial through the port 14, the short tube 18a, connecting tubes 16 and 32, the short tube 30, a space defined by the surface of the head 28a of the valve body 28 at the initial position and the cylindrical body 20, and the hollow needle 22. At this time, the transfusion liquid flows into the vial like a jet stream. The drug is more readily dissolved in the transfusion liquid by turn the bottom of the vial upward. The drug thus dissolved in the transfusion liquid is naturally returned to the bag 12 by releasing the pressure on the bag 12. By repeating these operations, all the drug is dissolved in the transfusion liquid, and the drug solution is returned to the bag 12. Thereafter, the cylindrical body 20 is held by a hand. Then, the drip chamber 40 is moved upward by another hand to cause the hollow needle 42a to pierce the movable valve body 28 and the head surface to abut against the inner surface of the upper end portion of the cylindrical body 20. Thus, the hollow needle 22 is closed by the side of the valve body 28, and the bag now containing the dissolved drug communicates with the drip chamber 40 through the needle 42a. Thereafter, the transfusion liquid containing the drug dissolved therein can be administered to a subject according to the usual transfusion operations.

Figure 2:
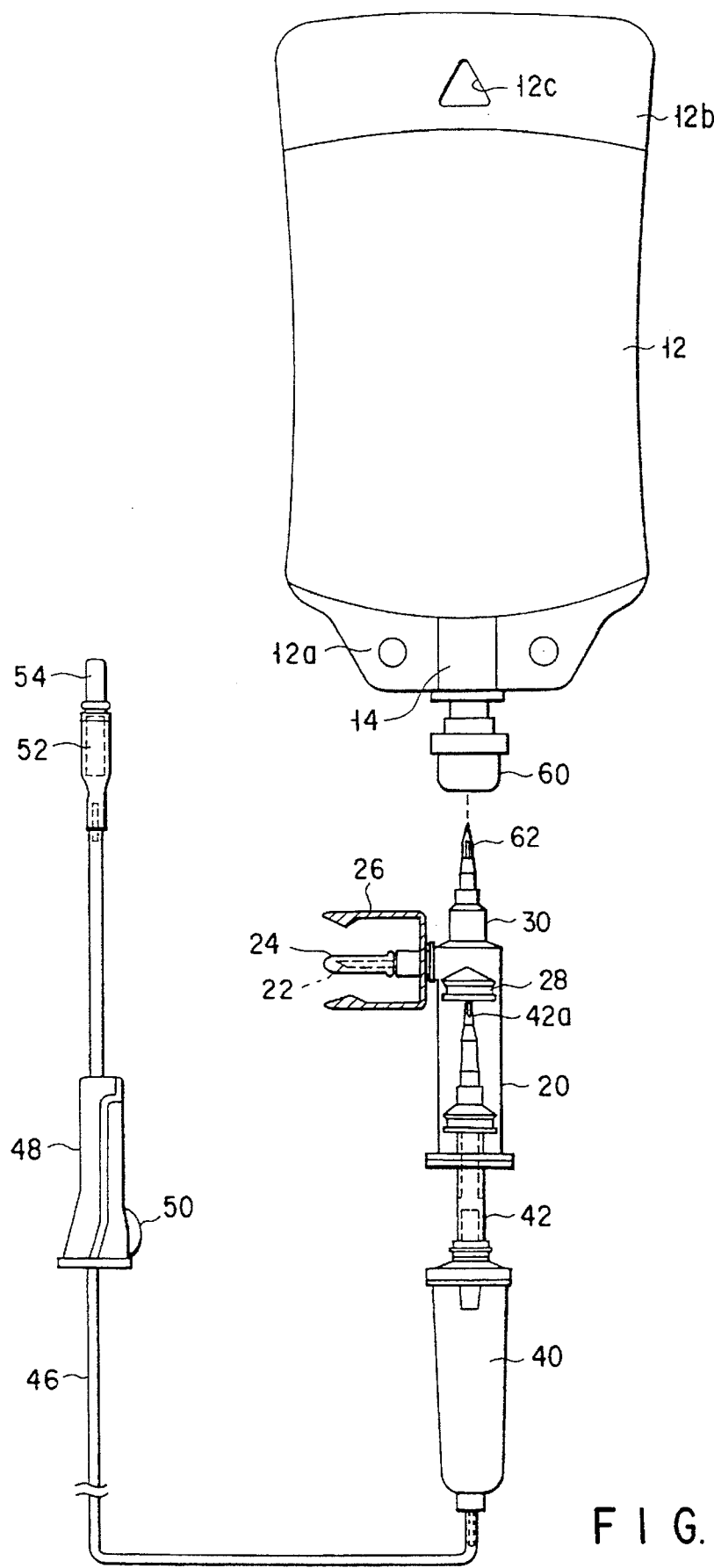
FIG. 2 schematically shows a drug delivery device according to a second embodiment of the present invention.

FIG. 2 shows a drug delivery device according to a second embodiment of the present invention. The device shown in FIG. 2 has the same construction as that of the device of FIG. 1, except that a hollow needle 62 is provided on the tip end portion of the short tube 30 which is provided on the cylindrical body 20, instead of the connecting tubes 16 and 31, and the communication mechanism 18. Further, a rubber cap 60 is provided on the port 14 of the bag 12. The hollow needle 62 is pierced into the rubber cap 60, instead of cutting off the communication mechanism 18 in FIG. 1.

As can be readily understood by those skilled in the art, the drug delivery device of FIG. 2 may be provided as a commercial product without the transfusion liquid bag 12.

FIG. 3 shows a drug delivery device according to a third embodiment of the present invention. This device has a flexible bottle 72 containing a transfusion liquid. The bottle 72 is constructed by a hollow cylindrical body portion 72a, and an inverted conical portion 72b formed integrally with the cylindrical portion 72a. At the transition portion of the body portion 72 to the conical portion 72b, a spiral groove 88 is formed which has a shape adapted to hold or accommodate a transfusion tube 85. The transfusion tube 85 is wound around the body portion 72 to be held by the groove 88, and held by a holder 89 which transverse the bundle of the tube 85. Thus, the dissolving operation is smoothly conducted without interfering with the long transfusion tube 85. At the tip end portion 72b of the bottle 72, a rubber stopper 90 which can be pierced by a needle is provided.

The device of FIG. 3 has a round hollow cylindrical body 77 generally made of a hard plastic material, and fitting over the rubber stopper 90. At the side of the cylindrical body 77, a hollow needle 75, like the hollow needle 22 of FIG. 1, is formed. The needle 75 pierces into the rubber stopper of the vial 74 (see FIG. 4) containing a drug to establish communication between the cylindrical body 77 and the vial 74. The hollow needle 75 may be covered by an elastic cap (not shown), as in the device of FIG. 1.

Around the hollow needle 75, a cup-shaped accommodating member 91, like the accommodating member 26 of FIG. 1, is provided for accommodating and holding the vial 74 when the vial is pierced by the needle 75.

A diaphragm 93 is formed across the cross-section of the cylindrical body 77 at a position above the hollow needle 75. A hollow needle 73 for piercing into the rubber stopper 90 penetrates the diaphragm 93.

Inside the cylindrical body 77, there is provided a movable valve body 76 having a side surface which can slidably contact the inner surface of the body 77. More specifically, the valve body 76 is formed of a hollow round cylinder having a relatively thick side wall which can close the needle 75, and has a relatively thin bottom wall which can be pierced by a needle. The movable valve body 76 is set at an initial position below the hollow needle 75 so as not to clog the hollow needle 75 by its side wall. A predetermined space 92 is defined between the bottom surface of the valve body 76 at the initial position and the bottom surface of the cylindrical body 77, while a space 94 is defined between the upper open end of the valve body at the initial position and the diaphragm 93 holding the hollow needle 73 for communication, through which space the needles 75 and 73 are communicated with each other. A hollow needle 80 formed at the upper portion of the drip chamber 79 so as to communicate with the drip chamber 79 penetrates the bottom wall of the cylindrical body 77 to extend into the space 92 just below the bottom wall 76a of the valve body 76. As in the device of FIG. 1, the drip chamber 79 is connected with the transfusion tube 85, and a roll clamp 84 is provided midway of the transfusion tube 85.

Further, around that portion of the rubber stopper 90 which is not covered by the cylindrical body 77, there is provided a stopper member 71 which can easily be removed. The stopper member 71 prevents the movement of the cylindrical body 77 toward the bottle 72. Likewise, a second stopper member 78 which can easily be removed is provided between the cylindrical body 77 and the drip chamber 79. The stopper member 78 prevents the movement of the drip chamber 79 toward the cylindrical body 77, that is, the further movement of the needle 80 into the cylindrical body 77.

Figure 4:
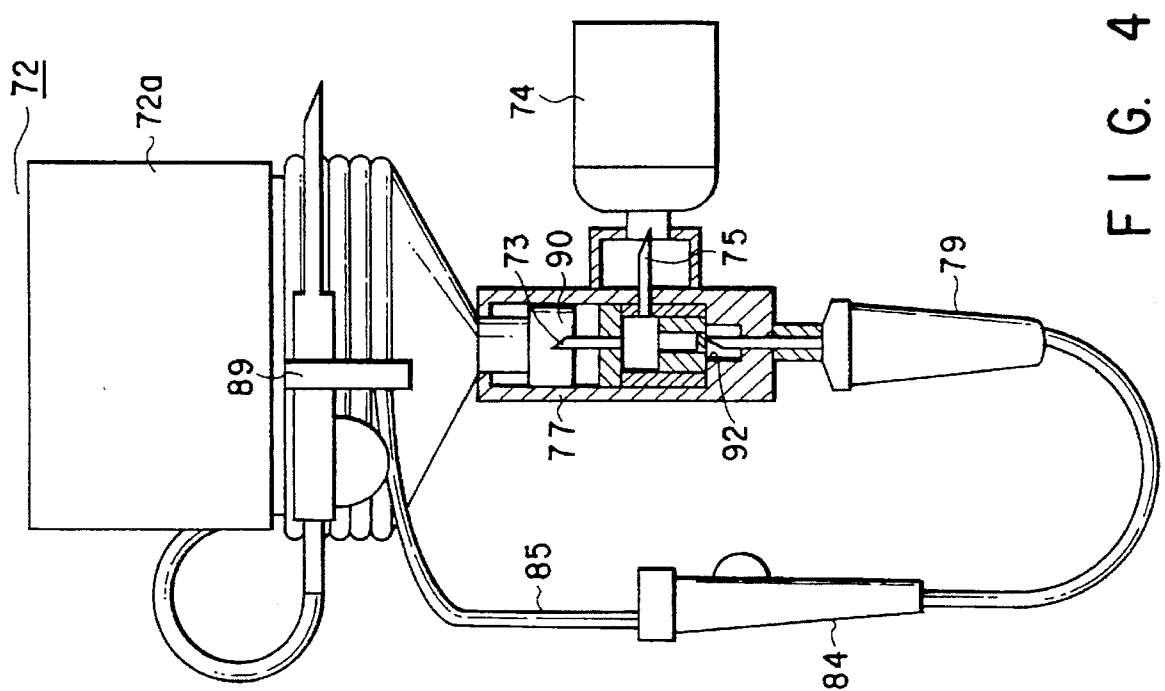
FIG. 4 shows the device of FIG. 3 in which a vial is accommodated.

To dissolve the powdery drug in the vial 74 in the transfusion liquid in the bottle 72, the vial 74 is accommodated in the accommodating member 91 and is pierced by the hollow needle 75, as shown in FIG. 4. Then, the stopper member 71 is removed, the cylindrical body 77 is held by one hand, and the bottle 72 is forced downwardly by another hand to cause the hollow needle 73 to pierce the rubber stopper 90. Thus, the bottle 72 communicates with the vial through the space 94. The needle 80 remains fixed at its initial position, and therefore the needle 80 does not communicate with the space 94. In this state, when the pressure is exerted on the bottle 72 from outside, for example by a hand, a portion of the transfusion liquid in the bottle is forced into the vial 74, and dissolve the powdery drug therein. When the vial 74 is turned upside down to release the pressure on the bottle 72, the drug solution in the vial 74 flows back into the bottle 72. By repeating the flowing-in operation of the transfusion liquid and the flowing-back operation of the drug solution, the drug in the vial 74 entirely dissolved in the transfusion liquid, and the whole solution flow into the bottle 72.

Figure 5:
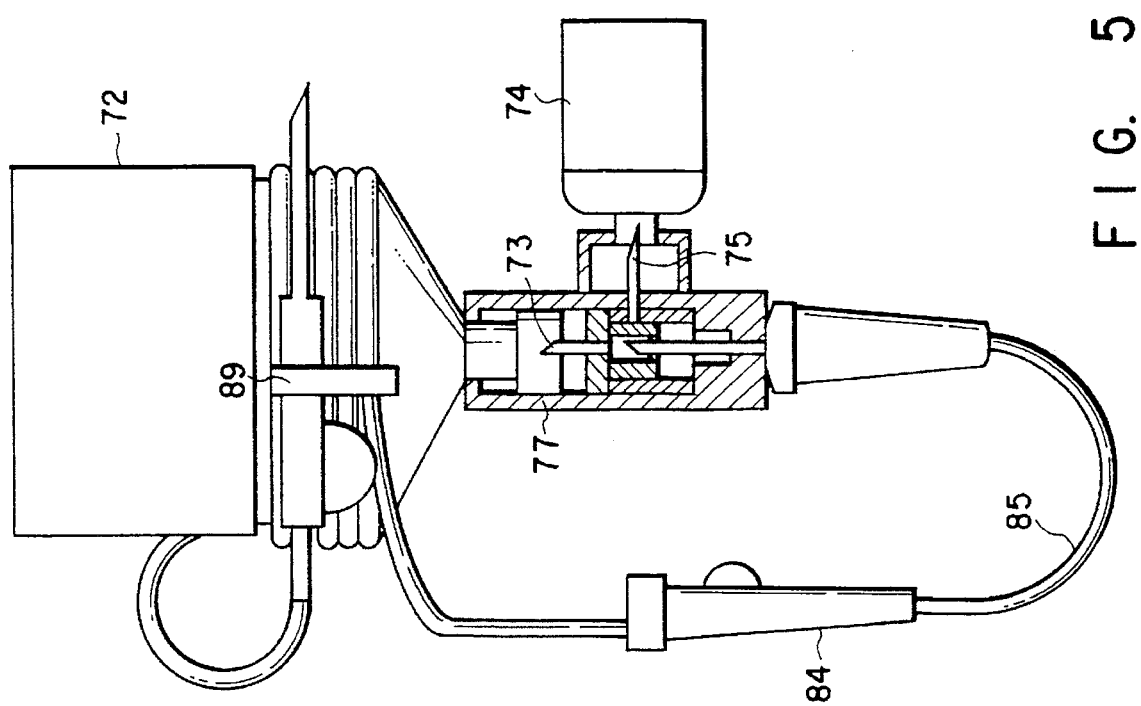
FIG. 5 shows the device of FIG. 4 in which a transfusion liquid bottle is communicated with a drip chamber.

Next, the stopper member 78 is removed, the drip chamber 79 is forced upward, while holding the cylindrical body 77 by a hand, to cause the hollow needle 80 to pierce the bottom wall of the valve body 76 and extend into the hollow portion 76a of the valve body 76, and to cause the valve body 76 to abut against the diaphragm 93. In this way, the vial needle 75 is closed by the side surface of the valve body 76. At the same time, the bottle 72 now containing the drug solution communicates with the drip chamber 79 through the hollow needle 73, the hollow portion 76a of the valve body 76 and the hollow needle 80 (see FIG. 5). In this state, the transfusion tube 85 is closed by the clamp 84, a portion of the transfusion liquid is introduced into the drip chamber 79 to the half volume of the chamber 79. When the roll clamp 84 is loosened, and a pressure is exerted on the bottle 72 from outside, the transfusion liquid flows from the bottle 72 in the transfusion tube 85 through the drip chamber 79. At this time, since the liquid surface in the drip chamber 79 is positioned below the needle 86, the air in the transfusion tube 85 is expelled upward, or toward the needle 86 side, leaving no air in the system downstream of the liquid surface in the drip chamber 79, thus filling the whole transfusion tube 85 with the transfusion liquid. Further, since the manifold 87 is face downward, the air in the manifold 87 is also expelled off, and discharged through the syringe needle 86. Incidentally, the groove 88 may be formed on the cylindrical body 77, instead on the bottle 72.

As has been described above, operations for dissolving the drug in the transfusion liquid and mixing it into the transfusion liquid can be greatly simplified, while maintaining the sterility according to the present invention.

What is claimed is:

1. A device for dissolving and delivering a drug in a transfusion liquid comprising:

a transfusion liquid container containing a transfusion liquid;

a drip chamber;

a transfusion tube communicating with the drip chamber;

a cylindrical body having first and second end portions, the first end portion of the cylindrical body being communicable with an inside of the transfusion liquid container, and the second end portion of the cylindrical body being communicable with the drip chamber;

a first hollow needle communicating with and projecting outwardly from the cylindrical body, the first hollow needle establishing communication between the transfusion liquid container and a drug container containing a drug to be introduced into the transfusion liquid, through the cylindrical body, by piercing into the drug container;

a drug container-accommodating body provided around the first hollow needle and outside the cylindrical body for accommodating the drug container;

a movable valve body having a side portion liquid tightly slidable on an inner surface of the cylindrical body, and being provided inside the cylindrical body at an initial position such that the first hollow needle is open, the movable valve body defining a space through which the transfusion liquid is introduced into the drug container to dissolve the drug when the cylindrical body communicates with the transfusion liquid container and the drug container is accommodated in the drug container-accommodating body and pierced by the first hollow needle; and a second hollow needle which communicates with the drip chamber and which is capable of advancing into the cylindrical body under sterile conditions, the second hollow needle establishing communication between the drip chamber and the transfusion liquid container by piercing the valve body after the dissolved drug is introduced into the transfusion liquid container, and moving the valve body from the initial position to a second position at which the first hollow needle is closed by the side portion of the valve body.

2. The device according to claim 1, wherein the side portion of the movable valve includes a plurality of annular ribs which slidably contact the inner surface of the cylindrical body.

3. The device according to claim 2, wherein the cylindrical body includes a first connecting tube on an upper end portion thereof, and the transfusion liquid container includes a second connecting tube, the first and second connecting tubes being joined under sterile conditions.

4. The device according to claim 3, wherein the second connecting tube includes a communicating mechanism which establishes communication between the transfusion liquid container and the cylindrical body.

5. The device according to claim 1, further comprising a sterility-maintaining gasket provided on a proximal end portion of the second hollow needle.

6. The device according to claim 1, wherein the cylindrical body includes a hollow needle member for establishing communication between the transfusion liquid container and the cylindrical body by piercing the transfusion liquid container.

7. The device according to claim 1, wherein the movable valve body comprises a hollow cylinder having an upper open end and a closed bottom end which are pierceable by the second hollow needle.

8. The device according to claim 7, wherein the transfusion liquid container includes means for accommodating the transfusion tube.

9. The device according to claim 7, wherein the cylindrical body includes means for accommodating the transfusion tube.

10. A device for dissolving and delivering a drug in a transfusion liquid comprising:

a drip chamber;

a transfusion tube communicating with the drip chamber;

a cylindrical body having first and second end portions, the first end portion of the cylindrical body being communicable with an inside of a transfusion liquid container containing a transfusion liquid, and the second end portion of the cylindrical body being communicable with the drip chamber;

a first hollow needle communicating with and projecting outwardly from the cylindrical body, the first hollow needle establishing communication between the transfusion liquid container and a drug container containing a drug to be introduced into the transfusion liquid, through the cylindrical body, by piercing into the drug container;

a drug container-accommodating body provided around the first hollow needle and outside the cylindrical body for accommodating the drug container;

a movable valve body having a side portion liquid tightly slidable on an inner surface of the cylindrical body, and being provided inside the cylindrical body at an initial position such that the first hollow needle is open, the movable valve body defining a space through which the transfusion liquid is introduced into the drug container to dissolve the drug when the cylindrical body communicates with the transfusion liquid container and the drug container is accommodated in the drug container-accommodating body and pierced by the first hollow needle; and a second hollow needle which communicates with the drip chamber and which is capable of advancing into the cylindrical body under sterile conditions, the second hollow needle establishing communication between the drip chamber and the transfusion liquid container by piercing the valve body after the dissolved drug is introduced into the transfusion liquid container, and moving the valve body from the initial position to a second position at which the first hollow needle is closed by the side portion of the valve body.

* * * * *